US011224702B2

(12) United States Patent
Esteve

(10) Patent No.: US 11,224,702 B2
(45) Date of Patent: Jan. 18, 2022

(54) SPRAY DISPENSER FOR NASAL DRUGS

(71) Applicant: AP PHARMA SYSTEMS ATOMIZADORES E DISPENSADORES LTDA, Porto Feliz (BR)

(72) Inventor: Victor Esteve, Itu (BR)

(73) Assignee: AP PHARMA SYSTEMS ATOMIZADORES E DISPENSADORES LTDA, Porto Feliz (BR)

( * ) Notice: Subject to any disclaimer, the term of this patent is extended or adjusted under 35 U.S.C. 154(b) by 177 days.

(21) Appl. No.: 15/576,183

(22) PCT Filed: May 12, 2016

(86) PCT No.: PCT/IB2016/000639
§ 371 (c)(1),
(2) Date: Nov. 21, 2017

(87) PCT Pub. No.: WO2016/198931
PCT Pub. Date: Dec. 15, 2016

(65) Prior Publication Data
US 2018/0133415 A1 May 17, 2018

(30) Foreign Application Priority Data
Jun. 12, 2015 (EP) .................................. 15 171 954

(51) Int. Cl.
*A61M 11/00* (2006.01)
*A61M 15/08* (2006.01)
(Continued)

(52) U.S. Cl.
CPC ......... *A61M 11/001* (2014.02); *A61M 11/008* (2014.02); *A61M 11/06* (2013.01);
(Continued)

(58) Field of Classification Search
CPC ........ A61M 11/00; A61M 11/001–008; A61M 11/02–08; A61M 13/00;
(Continued)

(56) References Cited

U.S. PATENT DOCUMENTS 5,497,944 A * 3/1996 Weston ............. A61M 15/0065
239/321
5,950,877 A * 9/1999 Garcia .................. A61M 15/08
222/190
(Continued)

FOREIGN PATENT DOCUMENTS

CN 1324257 A 11/2001
CN 101384373 A 3/2009
(Continued)

OTHER PUBLICATIONS

International Search Report and Written Opinion Form PCT/ISA/220, International Application No. PCT/IB2016/000639, pp. 1-8, International Filing Date May 12, 2016, dated Jul. 26, 2016.
(Continued)

*Primary Examiner* — Jan Christopher L Merene
*Assistant Examiner* — Ned T Heffner
(74) *Attorney, Agent, or Firm* — Bond Schoeneck & King, PLLC; George McGuire

(57) ABSTRACT

Spray dispenser for nasal drugs includes a non-pressurized bottle for storing medical fluids in particular of drugs and other sterile fluids, a mounting body mounted to the top of the bottle and an actuating body, wherein the bottle, the mounting body and the actuating body are aligned along a longitudinal axis, and wherein the actuating body is slideably attached to the mounting body along the longitudinal axis and movable between an actuating position and a non-actuating position, wherein the spray dispenser includes an applicator nozzle and an actuating section for moving the (Continued)

Figure 1:
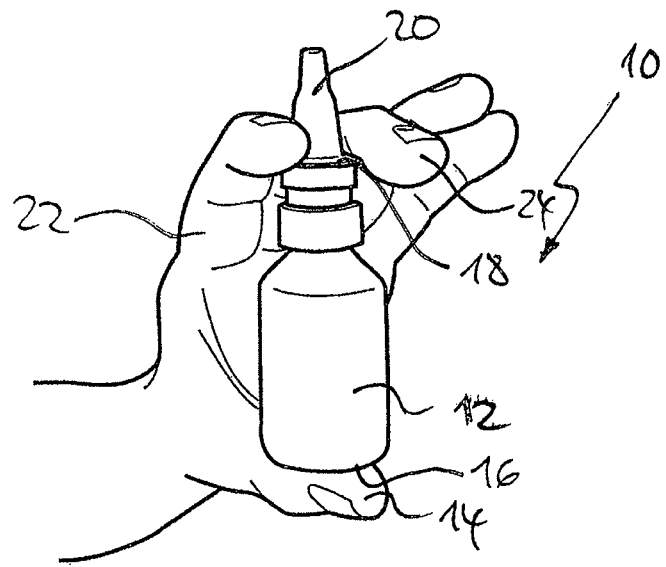

actuating body into the actuating position, characterized in that the applicator nozzle has a nozzle axis which is inclined with respect to the longitudinal axis, the applicator nozzle facing away from the actuating section.

8 Claims, 9 Drawing Sheets

(51) Int. Cl.
*B05B 11/00* (2006.01)
*A61M 11/06* (2006.01)
*B05B 15/40* (2018.01)
*A61M 39/24* (2006.01)

(52) U.S. Cl.
CPC ............ *A61M 15/08* (2013.01); *A61M 39/24* (2013.01); *B05B 11/0062* (2013.01); *B05B 11/0067* (2013.01); *B05B 11/00412* (2018.08); *B05B 11/3001* (2013.01); *B05B 15/40* (2018.02); *A61M 2039/248* (2013.01); *A61M 2039/2446* (2013.01); *A61M 2202/005* (2013.01); *A61M 2205/7536* (2013.01); *A61M 2240/00* (2013.01)

(58) Field of Classification Search
CPC .... A61M 15/00–0013; A61M 15/0028; A61M 15/0065–0078; A61M 15/0085; A61M 15/009–0098; A61M 15/06; A61M 15/08
See application file for complete search history.

(56) References Cited

U.S. PATENT DOCUMENTS

| | | | | |
|---|---|---|---|---|
| 6,145,703 | A * | 11/2000 | Opperman | ........ A61M 15/0065 222/82 |
| 6,332,561 | B1 * | 12/2001 | Garcia | ................ B05B 11/0005 222/321.3 |
| 2001/0004644 | A1 * | 6/2001 | Levin | ................... A61K 9/0043 514/646 |
| 2003/0053956 | A1 * | 3/2003 | Hofmann | ............. A61K 9/0043 424/45 |
| 2004/0068222 | A1 | 4/2004 | Brian | |
| 2011/0095053 | A1 | 4/2011 | Greiner-Perth et al. | |

FOREIGN PATENT DOCUMENTS

| | | |
|---|---|---|
| CN | 101385373 A | 3/2009 |
| CN | 202174028 U | 3/2012 |
| CN | 103118800 A | 5/2013 |
| CN | 203710486 U | 7/2014 |
| CN | 104058180 A | 9/2014 |
| CN | 104984447 A | 10/2015 |
| DE | 3525449 A1 | 1/1987 |
| DE | 69502295 T2 | 9/1998 |
| DE | 102006008874 A1 | 9/2007 |
| DE | 102007021415 A1 | 11/2008 |
| DE | 102007063213 B3 | 6/2009 |
| DE | 102013211423 A1 | 12/2014 |
| EP | 0170198 A2 | 2/1986 |
| EP | 0170198 B1 | 5/1990 |
| EP | 0487412 A1 | 5/1992 |
| EP | 2314380 B1 | 1/2015 |
| WO | 9718902 A1 | 5/1997 |
| WO | 102009040783 A1 | 3/2011 |
| WO | 2012001375 A1 | 1/2012 |

OTHER PUBLICATIONS

Non-translated Chinese Office Action, dated Feb. 3, 2020, pp. 1-7.
Non-tranlated EPO Communication, dated May 15, 2019. pp. 1-19.
Chinese Office Action, dated Dec. 16, 2020, pp. 1-7.

* cited by examiner

SPRAY DISPENSER FOR NASAL DRUGS

CROSS-REFERENCE TO RELATED APPLICATIONS

This application is the United States National Stage entry under 35 U.S.C. 371 of PCT/IB2016/000639, filed May 12, 2016, which claims priority to European application serial number 15171954.9, filed Jun. 12, 2015, the entire disclosure of each of which is incorporated herein by reference.

DESCRIPTION

The invention relates to a spray dispenser for nasal drugs comprising a non-pressurized bottle for storing medical fluids in particular of drugs and other sterile fluids, a mounting body mounted to the top of the bottle and an actuating body, wherein the bottle, the mounting body and the actuating body are aligned along a longitudinal axis, and wherein the actuating body is slideably attached to the mounting body along the longitudinal axis and movable between an actuating position and a non-actuating position, wherein the spray dispenser comprises an applicator nozzle and an actuating section for moving the actuating body into the actuating position.

Such spray dispensers are well known from the prior art and are also known as so-called atmospheric spray dispensers or non-pressurized spray dispensers. Such spray dispensers do not comprise a pressurized propellant gas which is needed for so-called aerosol type spray dispensers. Fluid is sprayed mechanically by use of different valve mechanisms providing for an exact dosage of the respective drugs. It is known for example to provide a metering valve for capturing a pre-defined dosage of a fluid to be dispensed during actuation of the respective spray dispenser which also comprises a spray valve for ejecting the fluid for example into the nose of a patient. Such spray valves eject the fluid as a spray in the dosage predefined by the metering valve in a previous actuation step wherein the metering valve is again actuated to provide a pre-defined dosage of the fluid.

Nevertheless, such atmospheric spray dispensers or non-pressurized spray dispensers known from the prior art are made for small volumes in the range 5 ml to 15 ml wherein the bottles of such spray dispensers is actuated by holding the bottle between the thumb which acts upon a bottom of the bottle and actuating the actuating section which has the form of an annular ring arranged concentrically to the vertical longitudinal axis and to the applicator nozzle with the index finger and the middle finger.

In clinical applications however, there is a need for spray dispensers having a bigger volume in the range of 50 ml to 200 ml.

Such spray dispensers having a volume in the range of 50 ml to 200 ml are known from the prior art and are usually pressurized spray dispensers having a bottle with a propellant gas and are therefore so-called aerosol dispensers. Such aerosol dispensers are usually having a circular cylindrical bottle which can be held in the hand between the thumb and the middle finger, ring finger and the pinkie finger wherein the index finger is used for actuation of the spray dispenser. EP 0 170 198 A2 discloses an applicator with such features.

Nevertheless, such large containers of pressurized spray dispensers for aerosol dispensers usually do not allow a calibration of the dosage which is possible with non-pressurized spray dispensers. Especially in clinical applications involving pediatric use, a predefined and calibrated dosage of the fluid or drug is important when moistening or sanitizing the nasal cavities in order to avoid a drowning sensation of a patient which can be caused due to excess fluid which can be released into the nasal cavities when using a pressurized spray dispenser or aerosol dispenser. Moreover, aerosol spray dispensers are quite expensive because of the aluminum which has to be used for the pressurized bottles.

It is therefore an object of the present invention to provide a cost effective spray dispenser for nasal drugs which provides for easy handling of large fluid volumes and for an exact dosage of the fluid or drug to be dispensed.

This object is solved by a spray dispenser according to the features of claim 1. The arrangement of the applicator nozzle in an inclined angle with respect to the longitudinal axis facing away from the applicator nozzle provides for the advantage that at the top of the spray dispenser more space can be provided for the actuating section which can then be actuated by a single finger such as the index finger while holding the bottle between the thumb and the middle finger, ring finger and the pinkie finger. It is particularly preferred if the bottle, the mounting body and the actuating body are made of plastic. Making those parts of plastic is much cheaper than aluminum which has to be used for pressurized bottles of aerosol spray dispensers.

According to a preferred embodiment of the spray dispenser, the actuating body comprises the applicator nozzle and the actuating section or a covering body is provided which is mounted on top of the actuating body, wherein the covering body comprises the applicator nozzle and the actuating section. In the case that the actuating body comprises the applicator nozzle and the actuating section, the actuating section is directly actuated by a finger of a user such as the index finger. In the case that a covering body is provided which is mounted on top of the actuating body, wherein the covering body comprises the applicator nozzle and the actuating section, the actuating body is indirectly actuated by pressing the actuating section of the covering body. The covering body is then displaced and acts upon the actuating body for moving the actuating body into the actuating position.

According to a preferred embodiment, the nozzle axis is inclined to the longitudinal axis in an angle in the range between about 30° to 60°, preferably in an angle of about 45°. Providing an angle in such a range allows for an easy handling of the spray dispenser wherein the applicator nozzle can be inserted into a nose of a patient easily.

It is particularly preferred that the actuating section is substantially perpendicular to the longitudinal axis and is arranged on a top side of the actuating body facing away from the bottle or on a top side of the covering body facing away from the bottle. The combination of an inclined applicator nozzle and an actuating section which is substantially perpendicular to the longitudinal axis is advantageous because such an actuating section can be easily operated with the index finger of the hand which is used to hold the bottle of the spray dispenser.

It is therefore particularly preferred if the actuating section is configured to be actuated by a single finger only. Therefore, it is particularly preferred if the actuating section is arranged at a radial small distance to the longitudinal axis such that no tilting effect occurs when actuating the spray dispenser with only one finger. It is also particularly preferred if the actuating section has a size sufficient to provide for an area of support for the finger actuating the spray dispenser. According to a preferred embodiment, the actuating section has a knurl or a corrugation which is configured such that slipping of a finger in case of a wet actuating section can be avoided.

According to an advantageous embodiment of the spray dispenser, the bottle has a volume in the range of about 50 ml to about 250 ml, preferably in the range of about 50 ml, to about 150 ml, more preferably about 100 ml. Such a high volume is particularly preferred in clinical applications where a high volume is needed to wash or treat nasal cavities.

According to the invention, the spray dispenser comprises a metering valve and a spray valve actuated by the actuating body. Providing a metering valve for capturing a pre-defined dosage of a fluid to be dispensed during actuation of the respective spray dispenser is important and advantageous because an overdosage of the drug to be dispensed or any drowning sensation felt by the patient can be avoided. More preferably, the dosage can be adjusted or calibrated according to the intended use of the spray dispenser.

In a particular advantageous embodiment for preservative-free formulations, the applicator nozzle comprises an anticontamination element having an antiinfective surface, preferably made of oligodinamic silver, arranged below the outlet of the applicator nozzle. Such an anticontamination element has an antibacterial effect and therefore any contamination or bacterial residue on the applicator nozzle can be avoided. Providing such an anticontamination element in applicator nozzles of a spray dispenser for nasal drugs is therefore very advantageous because contamination of the applicator nozzle which has to be inserted into a nose of a patient at least partially can be avoided.

According to the invention, a filter or filter matrix may be provided that is arranged between the bottle and the mounting body. Providing such a filter of filter matrix is particularly preferred in non-airless atmospheric or non-pressurized spray dispensers and allows for a safe air exchange between the interior of the bottle and the environment such that no vacuum is generated when actuating the spray dispensers.

It is particularly preferred if the filter is a ring filter or an insert filter.

According to the invention, a bag may be provided for storing the medical fluids, wherein the bag is disposed in an interior of the bottle and wherein a neck of the bag is sealingly connected to a neck of the bottle. Such a bag is preferably a pouch made of flexible polyethylene or surlyn. Preferably in that case the bottle is made of a rigid plastic material using a manufacturing process known as coex.

When providing a bag for storing the medical fluids, it is particularly preferred if the bottle comprises venting holes for air exchange with the interior of the bottle. Such spray dispensers are called airless spray dispensers because the fluid stored in the bag does not get in contact with air of the environment because the bag is collapsed because of the vacuum generated during each actuation step wherein the venting holes are provided for pressure equalization of the interior of the bottle with the environment such that the flexible bag is collapsed in the interior of the rigid bottle. Using a bag made of a flexible material for storing the liquid in the airless spray dispensers furthermore has the advantage that the spray dispenser can be used upside-down because no cannula has to be provided to suck in the fluid.

Further details and advantages of the invention can be taken from the following description, on the basis of which the embodiments of the invention that are represented in the figures are described and explained in more detail.

Figure 2:
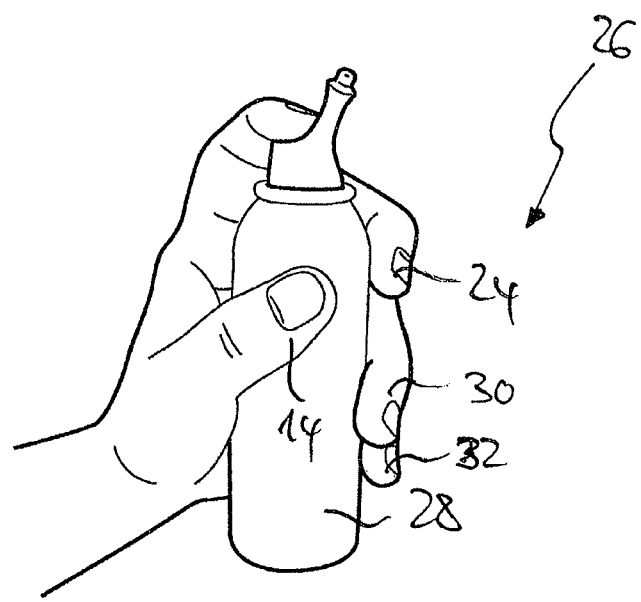
Figure 3:
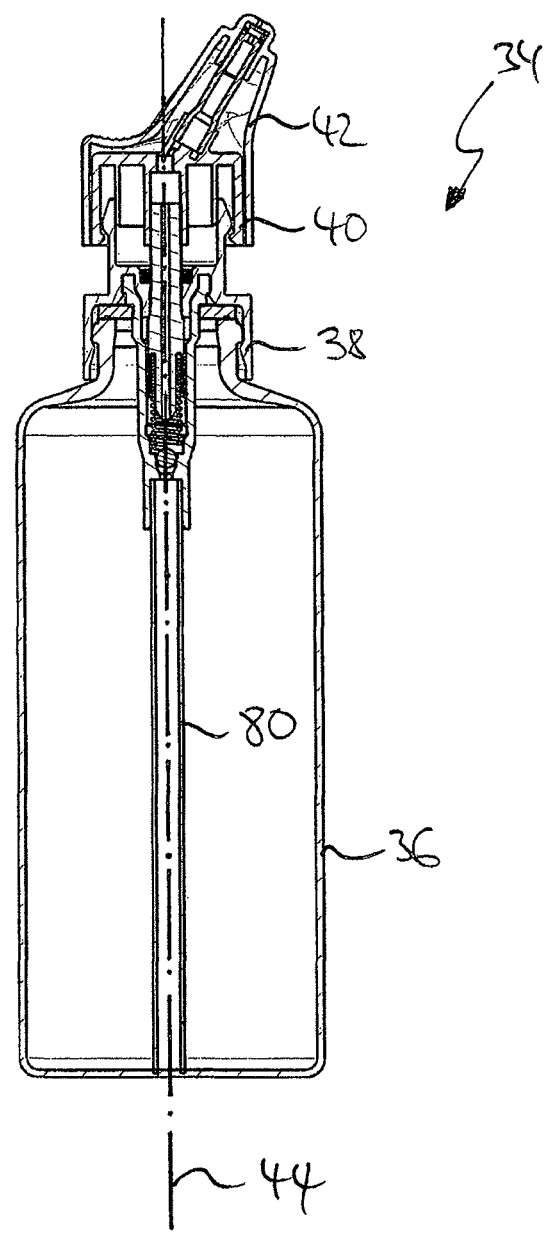
Figure 4:
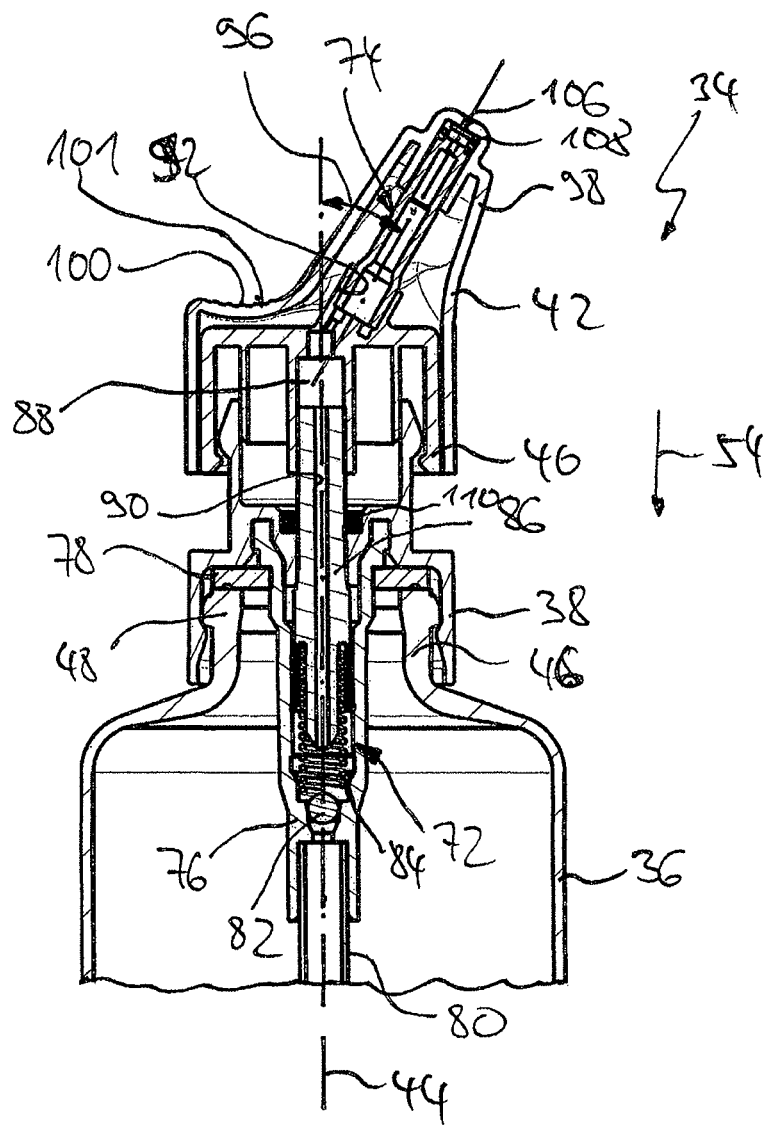
Figure 5:
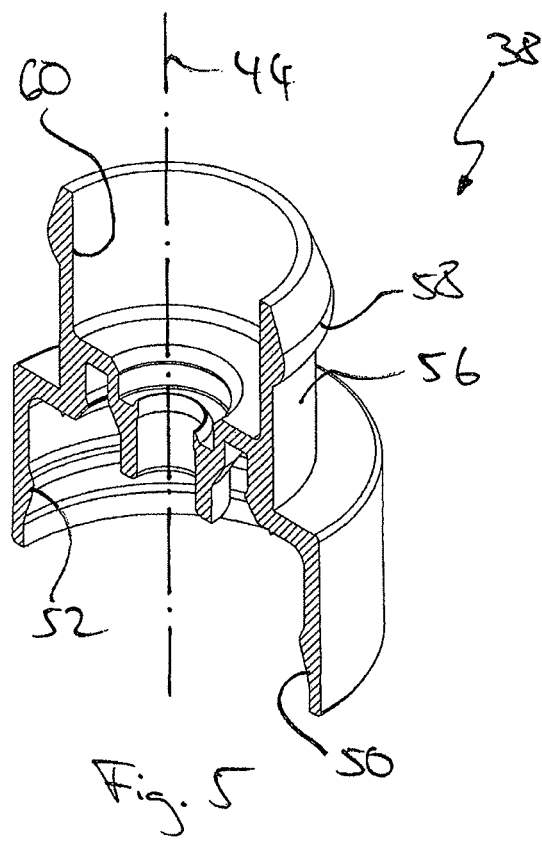
Figure 6:
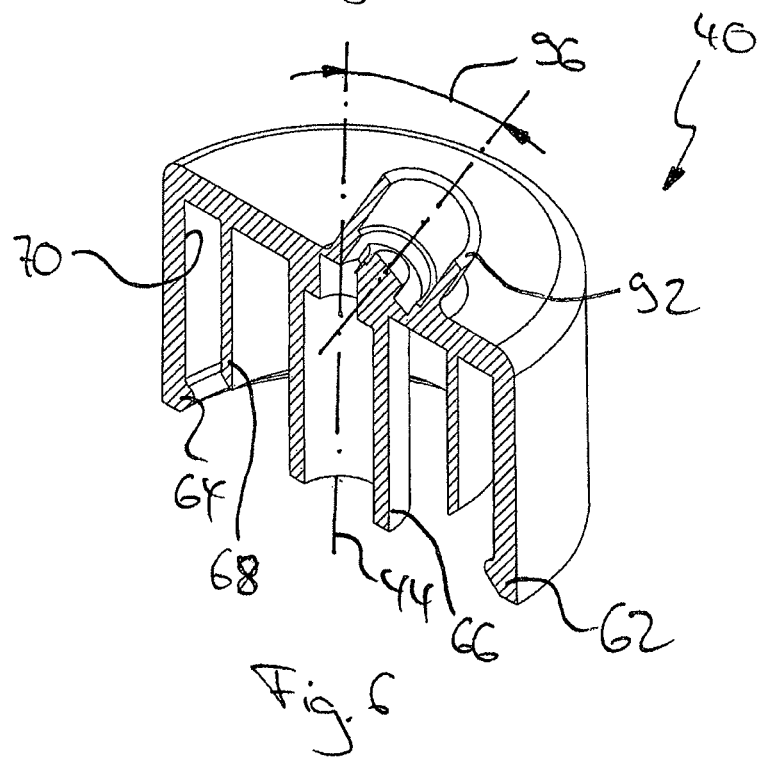

Respective figures are showing:

FIG. 1 a prior art non-pressurized spray dispenser;

FIG. 2 a prior art pressurized aerosol-type spray dispenser;

FIG. 3 a cross-section of a first embodiment of a spray dispenser according to the invention;

FIG. 4 an enlarged view of the top of the cross-section according to FIG. 3;

FIG. 5 a mounting body of the spray dispenser of FIGS. 3 and 4;

FIG. 6 an actuating body of the spray dispenser of FIGS. 3 and 4

Figure 7:
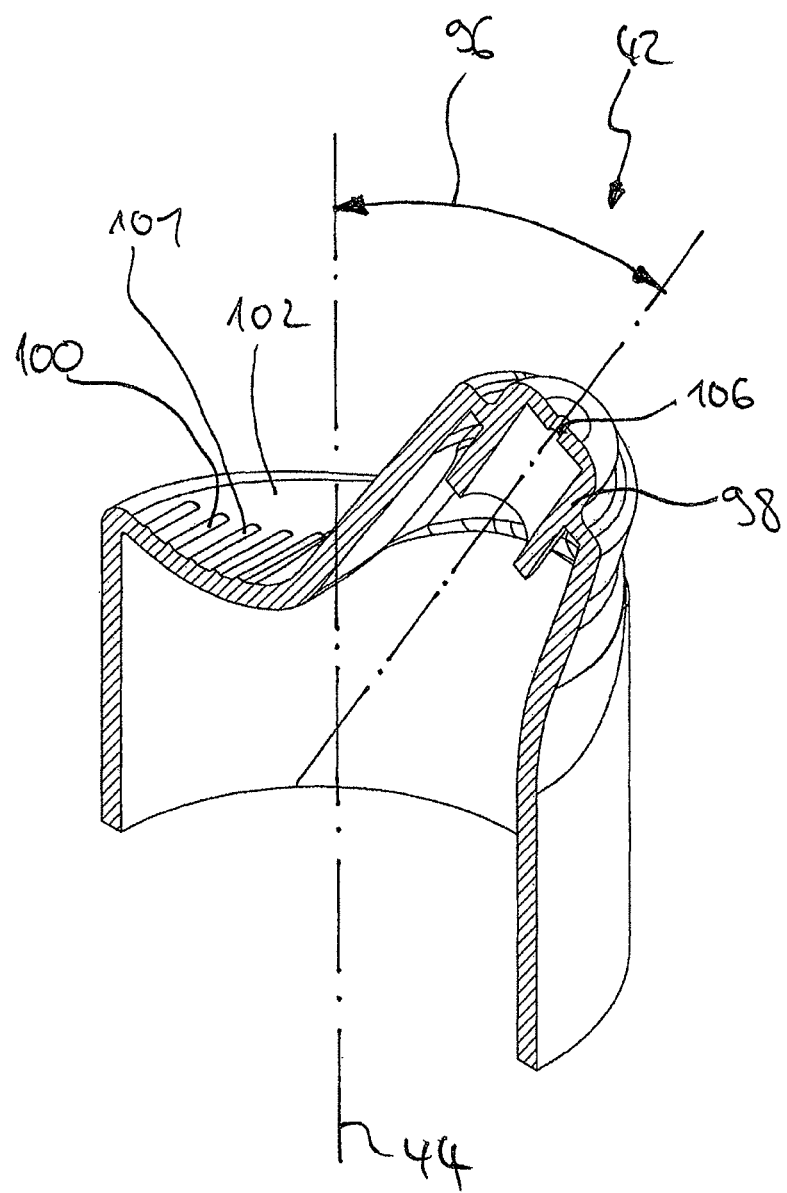

FIG. 7 a covering body of the spray dispenser of FIGS. 3 and 4; and

Figure 8:
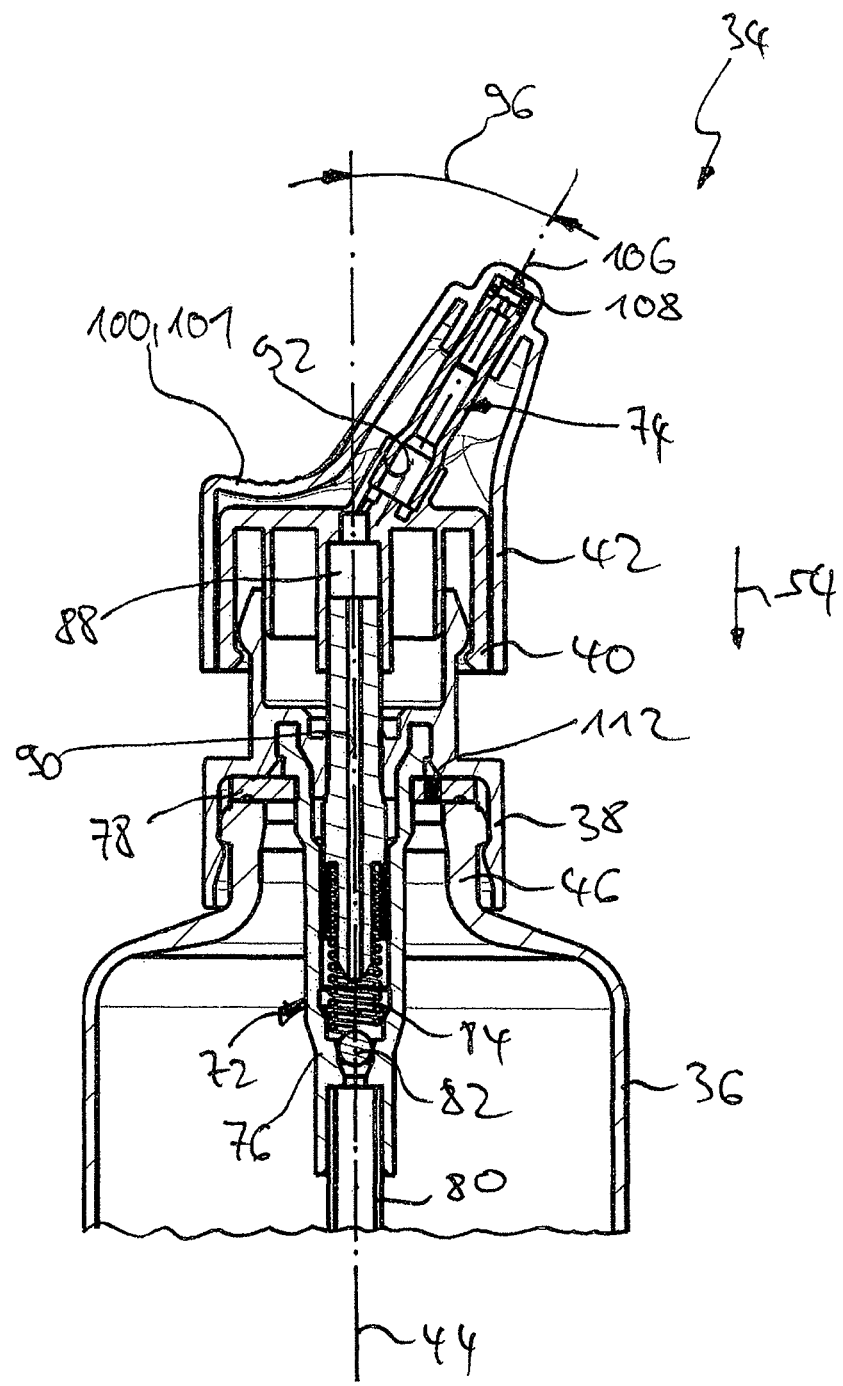
Figure 9:
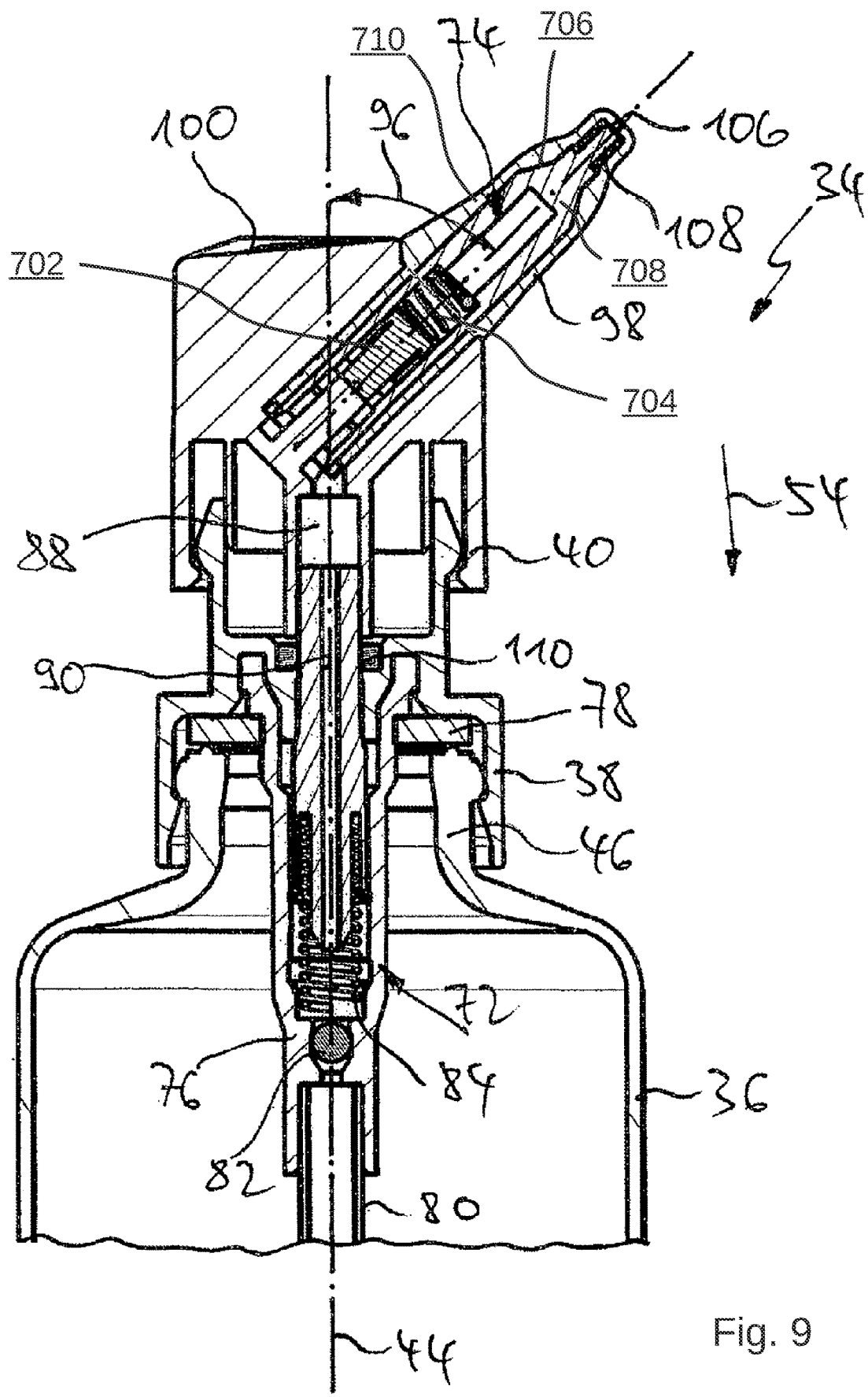
Figure 10:
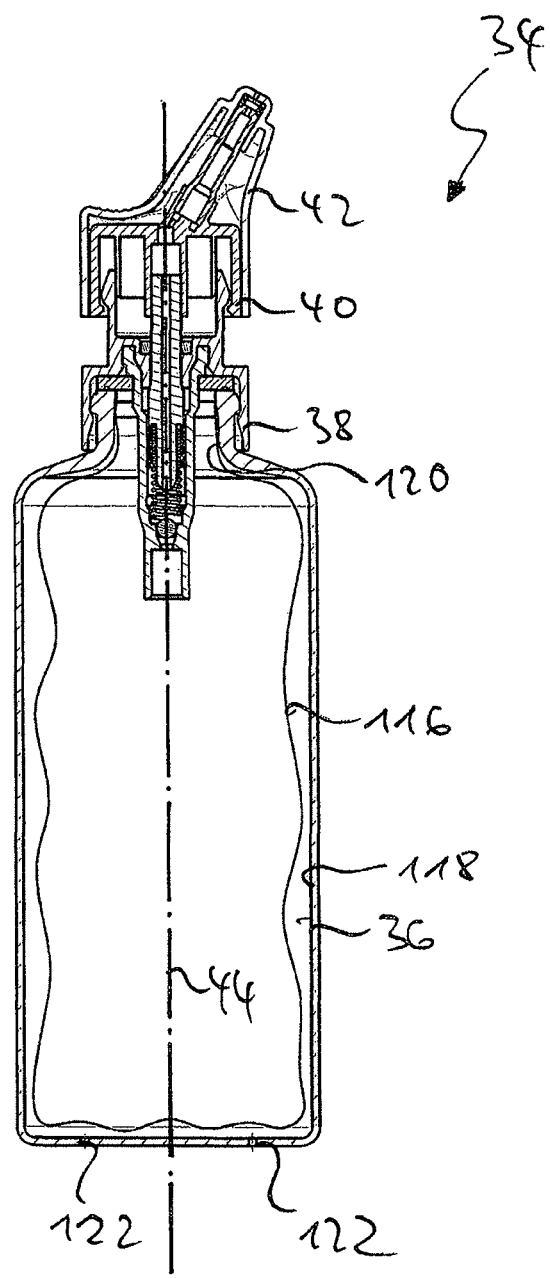
Figure 11:
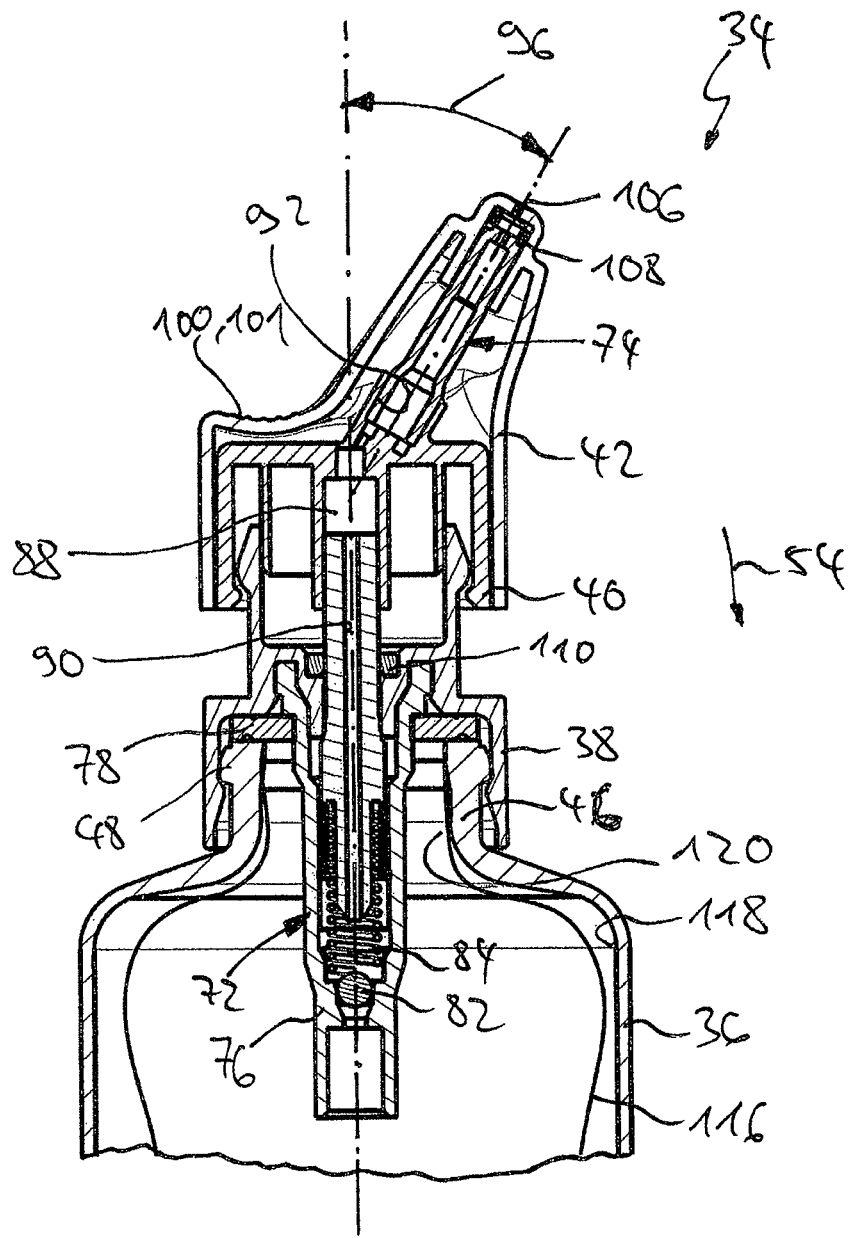

FIG. 8 an enlarged view of the top of a cross-section according a second embodiment of the invention;

FIG. 9 an enlarged view of the top of a cross-section according to a third embodiment of the invention;

FIG. 10 a cross-section of a fourth embodiment of a spray dispenser according to the invention; and FIG. 11 an enlarged view of the top of the cross-section according to FIG. 10.

FIG. 1 is showing a prior art non-pressurized spray dispenser 10. Such a spray dispenser 10 does not comprise a pressurized propellant gas which is needed for so-called aerosol type spray dispensers. The spray dispenser 10 sprays fluid mechanically by use of different valve mechanisms providing for an exact dosage of the respective drugs. Therefore, the spray dispenser 10 comprises a metering valve for capturing a pre-defined dosage of a fluid to be dispensed during actuation of the respective spray dispenser and also comprises a spray valve for ejecting the fluid for example into the nose of a patient. Such spray valves eject the fluid as a spray in the dosage predefined by the metering valve in a previous actuation step wherein the metering valve is again actuated to provide a pre-defined dosage of the fluid.

Such a prior art spray dispenser 10 or non-pressurized spray dispenser 10 is made for small volumes in the range 5 ml to 15 ml wherein the bottle 12 of such a spray dispenser 10 for nasal drugs is actuated by holding the bottle 12 between the thumb 14 which acts upon a bottom 16 of the bottle 12 and an actuating section 18 which has the form of an annular ring arranged concentrically to the vertical longitudinal axis and to the applicator nozzle with the index finger and the middle finger.

FIG. 2 is showing another prior art pressurized spray dispenser 26. Such a pressurized spray dispenser 26 has a volume in the range of 50 ml to 200 ml and is usually pressurized having a bottle 28 with a propellant gas and is therefore called aerosol dispenser. Such aerosol dispensers 26 are usually having a circular cylindrical bottle 28 which can be held in the hand between the thumb 14 and the middle finger 24, ring finger 30 and the pinkie finger 32 wherein only the index finger 22 is used for actuation of the spray dispenser 26.

Nevertheless, such a pressurized spray dispenser 26 does not allow a calibration of the dosage which is possible with a non-pressurized spray dispenser 10 of FIG. 1. Especially in clinical applications involving pediatric use, a predefined and calibrated dosage of the fluid or drug is important when moistening or sanitizing the nasal cavities of a patient in order to avoid a drowning sensation of the patient which can be caused due to excess fluid which can be released into the nasal cavities when using a pressurized spray dispenser 26 or aerosol dispenser 26.

FIG. 3 shows a section of a first embodiment of a spray dispenser 34 according to the invention wherein FIG. 4 shows an enlarged view of the top of the cross-section according to FIG. 3. The spray dispenser 34 comprises a bottle 36 for storing medical fluids in particular of drugs and other sterile fluids, a mounting body 38 mounted to the top of the bottle 36, an actuating body 40 and a covering body 42 mounted on top of the actuating body 40. The bottle 36, the mounting body 38, the actuating body 40 and the covering body 42 are arranged concentrically to a vertical longitudinal axis 44 of the spray dispenser 34.

The mounting body 38 is shown in an isolated view in FIG. 5, wherein the actuating body 40 is shown in an isolated view in FIG. 6 and wherein the covering body 42 is shown in an isolated view in FIG. 7. The spray dispenser 34 of FIGS. 3 and 4 will therefore be described with reference to FIGS. 3 to 7.

As described above, the spray dispenser 34 comprises a bottle 36 and a mounting body 38 mounted on top of the bottle 36. For mounting the mounting body 38 to the bottle 36, the bottle 36 which has a circular cylindrical form has a bottleneck 46 which has a protrusion 48 in the form of a ring protruding in the radial direction, i.e. perpendicular to the longitudinal axis 44. The mounting body 38 has a reception opening 50 for reception of the bottle neck 46 and comprises a protrusion 52 in the form of a ring protruding radially inside towards the longitudinal axis 44. The protrusion 48 and the protrusion 52 correspond to each other such that when the mounting body 38 is mounted on the bottleneck 46 of the bottle 36 and pressed in the direction of the longitudinal axis 44 along the direction of arrow 54, the protrusion 52 engages the protrusion 48 such that the mounting body 38 is fixedly connected to the bottle 36.

The mounting body 38 also comprises an annular ring 56 protruding in the direction of the longitudinal axis 44 facing away from the reception opening 50. The annular ring 56 has a protrusion 58 in the form of a ring protruding in the radial direction, i.e. perpendicular to the longitudinal axis 44. The annular ring 56 encloses a recess 60.

The actuating body 40 also comprises a radial outer annular ring 62 which is arranged concentrically to the longitudinal axis and having a protrusion 64 in the form of a ring protruding radially inside towards the longitudinal axis 44. The actuating body 40 furthermore has a radial inner annular ring 66 and a radial middle annular ring 68 both arranged concentrically to the longitudinal axis 44 wherein the radial middle annular ring 68 is disposed between the radial inner annular ring 66 and the radial outer annular ring 62. Between the radial outer annular ring 62 and the radial middle annular ring 68, an annular recess 70 is provided which is configured to receive the annular ring 56 of the mounting body 38 when the actuating body 40 is mounted on the mounting body 38. When mounting the actuating body 40 on the mounting body 38 by pressing it in the direction of the longitudinal axis 44 in the direction of the arrow 54, the protrusion 64 engages the protrusion 58 such that the actuating body 40 is slideably attached to the mounting body 38 along the longitudinal axis 44 and movable between a lower actuating position and an upper non-actuating position.

The spray dispenser 34 comprises a metering valve 72 for capturing a pre-defined dosage of a fluid to be dispensed during actuation of the spray dispenser 34 and also comprises a spray valve 74 for ejecting the fluid for example into the nose of a patient.

The metering valve 72 comprises a base part 76 mounted between a disk-like intermediate member 78 disposed between the bottle 36 and the mounting body 38 and a recess 80 in the mounting body 38. The base part 76 has a sleeve-like form and extends concentrically to the longitudinal axis 44 wherein a part of the base part 76 extending into the bottle 36 has a cannula 80 which acts as an intake for the fluids or drugs to be dispensed by the spray dispenser 34.

In the interior of the base part 76 a ball like valve member 82 is disposed which prevents reflux of the fluid pre-dosed by the metering valve 72. Furthermore, a helical spring 84 and a cannula like valve member 86 are arranged in the interior of the base part 76 wherein the valve member 86 is supported by the spring 84 and pretensioned to the top against the direction of the arrow 54. When the actuating body 40 is moved into the actuating position along the longitudinal axis 44 in the direction of arrow 54, the valve member 86 is pressed downwards against the valve member 76 against the force of the spring 84. When the actuating body 40 is moved back into the non-actuating position by the force of the spring 84, a vacuum is generated in dosing-room 88 and a predefined dosage of fluid is sucked into the dosing room 88 through the cannula 80 and a through-hole 90 in the valve member 76.

Therefore, the subject spray dispenser 34 allows for providing a predefined dosage of a fluid or drug by use of the metering valve 72.

The actuating body 40 furthermore comprises an annular protrusion 92 for accommodation of the spray valve 74. The protrusion 92 has a central nozzle axis 94 which is inclined with respect to the longitudinal axis 44 in an angle 96 of about 45°. When the actuating body 40 is moved into the actuating position along the longitudinal axis 44 in the direction of arrow 54 and a predefined dosage of fluid has already been sucked into the dosing room 88 through the cannula 80 and the through-hole 90 in the valve member 76 in a previous actuating step, the dosing room 88 is compressed and fluid is sprayed by the spray valve 74.

In the embodiment of FIGS. 3 to 7, the actuating body 40 is covered by a covering body 42 which comprises an applicator nozzle 98 and an actuating section 100 as shown in FIGS. 3 and 7. The actuating section 100 is substantially perpendicular to the longitudinal axis 44 and is arranged on a top side 102 of the covering body 42 facing away from the bottle 36 and is configured to be actuated by a single finger such as an index finger 22. The actuating section 100 has a corrugation 101 which is configured such that slipping of a finger 22 in case of a wet actuating section 100 can be avoided.

On the interior, the covering body 42 comprises a circular recess 104 for a part of the spray valve 74 arranged in the applicator nozzle 98 below an outlet opening 106 of the applicator nozzle 98. In the recess 104, an anticontamination element 108 is provided. Such an anticontamination element 108 has an antibacterial effect and therefore any contamination or bacterial residue on the applicator nozzle 98 can be avoided. Providing such an anticontamination element 108 in applicator nozzles 98 of a spray dispenser 34 for nasal drugs is therefore very advantageous because contamination of the applicator nozzle 98 which has to be inserted into a nose of a patient at least partially can be avoided.

The spray dispenser 34 of FIGS. 3 to 7 is a so-called non-airless spray dispenser 34. In order to avoid the generation of a vacuum in the bottle 36 after actuation, a filter or filter matrix 110 is provided between the valve member 76 and the mounting body 38. The filter matrix 110 prevents the leakage of fluids but is permeable to air such that a vacuum in the bottle 36 can be avoided.

FIG. 8 shows an enlarged view of the top of a cross-section according a second embodiment of the spray dispenser 34. Like elements are denoted the same reference numerals as in FIGS. 3 to 7. The spray dispenser 34 of FIG. 8 differs from the spray dispenser 34 of FIGS. 3 to 7 in that a filter 112 is inserted into the disk-like intermediate member 78 which has basically the same purpose as the filter matrix 110 of FIGS. 3 to 7.

FIG. 9 shows an enlarged view of the top of a cross-section according to a third embodiment of the spray dispenser 34. Like elements are denoted the same reference numerals as in FIGS. 3 to 8. The spray dispenser 34 of FIG. 9 differs from the spray dispensers of FIGS. 3 to 8 in that no covering body 42 is provided wherein the actuating body 40 comprises the applicator nozzle 98 and the actuating section 100. Since no covering body 42 is provided, the applicator nozzle 98 is a part of a spray valve unit 114 inserted into the actuating body 40 in an angle 96 with respect to the longitudinal axis 44 of about 45°. In the inside of the spray valve unit 114 an antibacterial anticontamination element 108 is arranged below the outlet 106.

FIG. 10 shows a cross-section of a fourth embodiment of a spray dispenser 34 according to the invention wherein FIG. 11 shows an enlarged view of the top of the cross-section. In contrast to the spray dispensers 34 of FIGS. 3 to 9 which are non-airless spray dispensers 34 and allow the fluid in the bottle 36 to get into contact with air by use of the filters 110, 112, the spray dispenser 34 of FIGS. 10 and 11 is a so-called airless spray dispenser 34. Like elements are denoted the same reference numerals as in FIGS. 3 to 9.

The spray dispenser 34 of FIGS. 10 and 11 differs from the spray dispensers of FIGS. 3 to 9 in that the fluid is not directly stored in the bottle 36. The spray dispenser 34 comprises a bag 116 for storing the medical fluids, wherein the bag 116 is disposed in an interior 118 of the bottle 36 and wherein a neck 120 of the bag 116 is sealingly connected to the neck 46 of the bottle 34. The bottle 36 furthermore comprises venting holes 122 for air exchange of the environment with the interior of the bottle 36.

Such spray dispensers 34 are called airless spray dispensers 34 because the fluid stored in the bag 116 does not get in contact with air of the environment because the bag 116 is collapsed because of the vacuum generated during each actuation step wherein the venting holes 122 are provided for pressure equalization of the bottle 36 such that the flexible bag 116 can be collapsed in the interior 118 of the rigid bottle 36.

What is claimed is:

1. A spray dispenser for nasal drugs comprising a non-pressurized bottle for storing medical fluids, a mounting body mounted to the top of the bottle and an actuating body, wherein the bottle, the mounting body and the actuating body are aligned along a longitudinal axis, and wherein the actuating body is slideably attached to the mounting body along the longitudinal axis and movable between an actuating position and a non-actuating position, wherein the spray dispenser comprises an applicator nozzle and an actuating section for moving the actuating body into the actuating position, wherein the applicator nozzle has a nozzle axis which is inclined with respect to the longitudinal axis in an angle, the applicator nozzle, the applicator nozzle facing away from the actuating section; wherein the spray dispenser comprises a metering valve for capturing a predefined dosage of fluid to be dispensed during actuation of the spray dispenser, a part of the base part extends into the bottle and has a cannula which acts as an intake for the medical fluids to be dispensed by the spray dispenser,
the spray dispenser comprises a spray valve for ejecting fluid, the spray valve actuated by the actuating body, the actuating body is covered by a covering body,
the covering body comprises a recess for a part of the spray valve arranged in the applicator nozzle below an outlet opening of the applicator nozzle,
the actuating body comprises a protrusion with the inclined nozzle axis, the protrusion accommodating the spray valve, wherein
a) a filter or filter matrix is arranged between the bottle and the mounting body.

2. The spray dispenser according to claim 1, characterized in that the covering body is mounted on top of the actuating body, wherein the covering body comprises the applicator nozzle and the actuating section.

3. The spray dispenser-according claim 1 characterized in that the actuating section is substantially perpendicular to the longitudinal axis and is arranged on a top side of the actuating body facing away from the bottle or on a top side of the covering body facing away from the bottle.

4. The spray dispenser according to claim 1, characterized in that the actuating section is configured to be actuated by a single finger.

5. The spray dispenser according to claim 1, characterized in that the bottle has a volume in the range of 50 ml to about 250 ml.

6. The spray dispenser according to claim 1, characterized in that the applicator nozzle comprises the outlet and an anticontamination element having an antiinfective surface arranged below the outlet of the applicator nozzle.

7. The spray dispenser according to claim 1, comprising a filter and characterized in that the filter is selected from a group consisting of a ring filter and an insert filter.

8. The spray dispenser according to claim 1, characterized in that the bottle comprises venting holes for air exchange with the interior of the bottle.

* * * * *